US012318204B2

United States Patent
Dong et al.

(10) Patent No.: US 12,318,204 B2
(45) Date of Patent: Jun. 3, 2025

(54) METHOD AND APPARATUS FOR COLLECTING AND ANALYZING URINE SAMPLES

(71) Applicants: Cao Dong, Milpitas, CA (US); Long Di, San Jose, CA (US); Cheng Yang, Lexington, MA (US); Longze Chen, Palmyra, VA (US)

(72) Inventors: Cao Dong, Milpitas, CA (US); Long Di, San Jose, CA (US); Cheng Yang, Lexington, MA (US); Longze Chen, Palmyra, VA (US)

(*) Notice: Subject to any disclaimer, the term of this patent is extended or adjusted under 35 U.S.C. 154(b) by 0 days.

(21) Appl. No.: 18/857,510

(22) PCT Filed: Apr. 17, 2023

(86) PCT No.: PCT/US2023/065848
§ 371 (c)(1),
(2) Date: Oct. 17, 2024

(87) PCT Pub. No.: WO2023/205604
PCT Pub. Date: Oct. 26, 2023

(65) Prior Publication Data
US 2025/0120634 A1    Apr. 17, 2025

Related U.S. Application Data

(60) Provisional application No. 63/363,128, filed on Apr. 18, 2022.

(51) Int. Cl.
*A61B 5/20* (2006.01)
*E03D 9/00* (2006.01)
*G01N 33/493* (2006.01)

(52) U.S. Cl.
CPC ............... *A61B 5/207* (2013.01); *E03D 9/00* (2013.01); *G01N 33/493* (2013.01)

(58) Field of Classification Search
CPC ......... A61B 5/207; E03D 9/00; G01N 33/493
See application file for complete search history.

(56) References Cited

U.S. PATENT DOCUMENTS 3,571,817 A * 3/1971 Gosnell ............... A61B 10/007
4/144.1
3,589,378 A   6/1971 Swanson et al.
(Continued)

FOREIGN PATENT DOCUMENTS

CN          110286001 A * 9/2019 ............. A47K 13/24

OTHER PUBLICATIONS

CN-110286001-A (Year: 2019).*

Primary Examiner — Kristina M Deherrera
Assistant Examiner — Fatemeh Esfandiari Nia
(74) Attorney, Agent, or Firm — Altman & Martin; Steven K Martin

(57) ABSTRACT

A urine collecting and analyzing apparatus for a toilet, the apparatus including a housing with a seat riser that mounts to the toilet rim and a measurement chamber that extends downwardly into the bowl, a urine collecting basin, a flushing system to clean the apparatus, and a controller for data processing and transmission. The basin has a bowl shape to collect urine for testing and is composed of two side panels or two side panels and a front panel. The panels are moved between a storage position along the housing and a collecting position forming the basin by a motorized mechanism. A transfer tube with a flow rate sensor and pump connects the basin to the measurement chamber. The flushing system feeds water through a flushing tube into the basin through an array of nozzles and cleans the entire surface of the basin.

30 Claims, 18 Drawing Sheets

(56) References Cited

U.S. PATENT DOCUMENTS

| | | | | |
|---|---|---|---|---|
| 5,730,149 | A | * | 3/1998 | Nakayama ............ G01N 33/493 |
| | | | | 600/584 |
| 2013/0053729 | A1 | * | 2/2013 | Stevic-Wages ...... A61B 10/007 |
| | | | | 600/584 |
| 2017/0114531 | A1 | * | 4/2017 | Ye ........................... E03D 11/02 |
| 2019/0046164 | A1 | | 2/2019 | Kramer et al. |
| 2020/0205717 | A1 | * | 7/2020 | Yang ....................... E03D 11/13 |

* cited by examiner

METHOD AND APPARATUS FOR COLLECTING AND ANALYZING URINE SAMPLES

TECHNICAL FIELD

The present invention relates to biomonitoring, medical measurements, and digital health, more particularly, to devices and methods for detecting medically relevant urine analytes and managing the collected data to assess a user's health status.

BACKGROUND ART

Digital health technologies such as smart and wearable devices with integrated computational analysis techniques provide an emerging approach to aid users and their healthcare providers in managing a potential illness more efficiently and promoting health outcomes. The examination of human excreta such as urine has been recognized as providing critical health information and insights. The measurement of urine analytes and biomarkers may be used for health assessment, disease diagnosis, and chronic disease management. Unlike blood-based testing, urine-based testing provide a non-invasive, fast, and accurate detection of biomarkers and bio-indicators.

The current standard of care utilizes the urinalysis strip, the urine dipstick, for urinary testing. Such tests require a complex manual urine collection process wherein the specimen can easily be contaminated. In addition, this complexity limits the user's willingness to take the urine test in outpatient settings. Such tests cause the lack of momentum of self-testing and report and consequently, lack of consistency of testing on a regular basis by users. Longitudinal results are missing, which dramatically reduces the clinical value.

The most cutting-edge solution in the industry is to provide a consolidated all-in-one toilet system to replace the existing traditional toilet. The bulky toilet system needs a considerable initial investment, and the bathroom's potential redesign and professional installation require a significant amount of work and cost.

Thus, there is a need for a user-friendly urine measurement device and method with a passive urine collection functionality and health data analysis that can be seamlessly integrated into an existing toilet with universal compatibility.

DISCLOSURE OF THE INVENTION

The present invention is a urine collecting and analyzing apparatus that mounts to a standard toilet. The apparatus includes a housing with a seat riser and a measurement chamber, a urine collecting basin, a flushing system to clean the apparatus, and a controller for data processing and transmission. The housing either mounts to or is integrated into the rim of the toilet bowl.

Optionally, a set of toilet seat and cover is provided. Optionally, they can provide further height and attitude adjustment over a typical seat and cover. Optionally, cushions integrated into the bottom of the seat can be inflated/deflated independently to adjust the attitude of the seat.

The measurement chamber extends downwardly from the bottom of the riser along the toilet bowl.

The urine collecting basin has a bowl shape to collect urine for testing. The basin slopes downwardly to the center and front so that the urine flows to an opening at the front of the basin. The basin is composed of two side panels or two side panels and a front panel.

The current invention contemplates four different configurations for storing the side panels. In the lower pivot configuration, the two side panels pivot on axles between the storage position against the inner surface of the housing and the collecting position below the housing. In the upper pivot configuration, the two side panels pivot on axles between the storage position against the inner surface of the housing and the collecting position just below the riser. In the side sliding configuration, the two side panels slide between the storage position against the inner surface of the housing and the collecting position below the housing. In the bottom sliding configuration, the two side panels slide between the storage position against bottom of the housing and the collecting position below the housing. The front panel rotates between the storage position and collecting position on pivot points. Rubber seals affixed to the edges of the panels seal the panels when in the collecting position.

A transfer tube connects the basin to the measurement chamber. A flow rate sensor and a pump are in-line with the transfer tube. The measurement chamber has an overflow outlet to discharge excessive urine and a drain in the floor for draining the chamber into the toilet bowl when testing is complete. Various sensors dip into the urine collected in the chamber for measurements.

The apparatus has a flushing system that flushes water through the system to remove any contaminants that may be present. The flushing system includes a water inlet connected to a water source. The inlet directly feeds a flushing valve that connects to a flushing tube that feeds water to flushing nozzles. During flushing, water is fed through the flushing tube into the basin through the array of flushing nozzles and cleans the entire surface of the basin. To further enhance cleaning, an optional detergent canister is attached to the flushing system, typically at the flushing valve.

At the beginning of the operation, the system controller optionally determines who the user is. After the user is identified, the controller instructs the basin mechanism to move the basin panels to the collecting position to form the basin and then activate the pump. As the user urinates, the pump feeds the urine from the basin to the measurement chamber. The controller calculates the urine volume from the flow rate sensor data. Once urine reaches the minimum volume for testing, the controller starts reading the sensors. After the desired sensor data is acquired, the controller processes the data and stores the results.

After the data processing is complete, the controller informs the user that the toilet can be flushed and then the flushing system is initiated. The measurement chamber drain is opened and the flushing valve is opened. If the apparatus includes the detergent canister, the detergent valve is opened. Pressure from the water source mixes the detergent and pushes the water through the flushing tube to the flushing nozzles. After a predetermined period, the detergent valve is closed. Meanwhile, the water from the flushing nozzles cleans the basin. The pump sends the water through the transfer tube into the measurement chamber, thereby cleaning the pump, flow sensor, transfer tube, and measurement chamber. After a preset period, the flushing valve is closed and the remaining water flows through the flushing system. The pump is stopped and the controller keeps the drain open to permit the remaining water to fully drain and then closes the drain.

After the flushing system is finished, the controller triggers the basin mechanism to retract the basin panels to their storage positions. The apparatus is deactivated and enters standby mode waiting for the next use.

When the controller finishes processing the data, it sends the assessment results to an app on an external device.

Objects of the present invention will become apparent in light of the following drawings and detailed description of the invention.

BRIEF DESCRIPTION OF DRAWINGS

For a fuller understanding of the nature and object of the present invention, reference is made to the accompanying drawings, wherein.

BEST MODES FOR CARRYING OUT THE INVENTION

Figure 1:
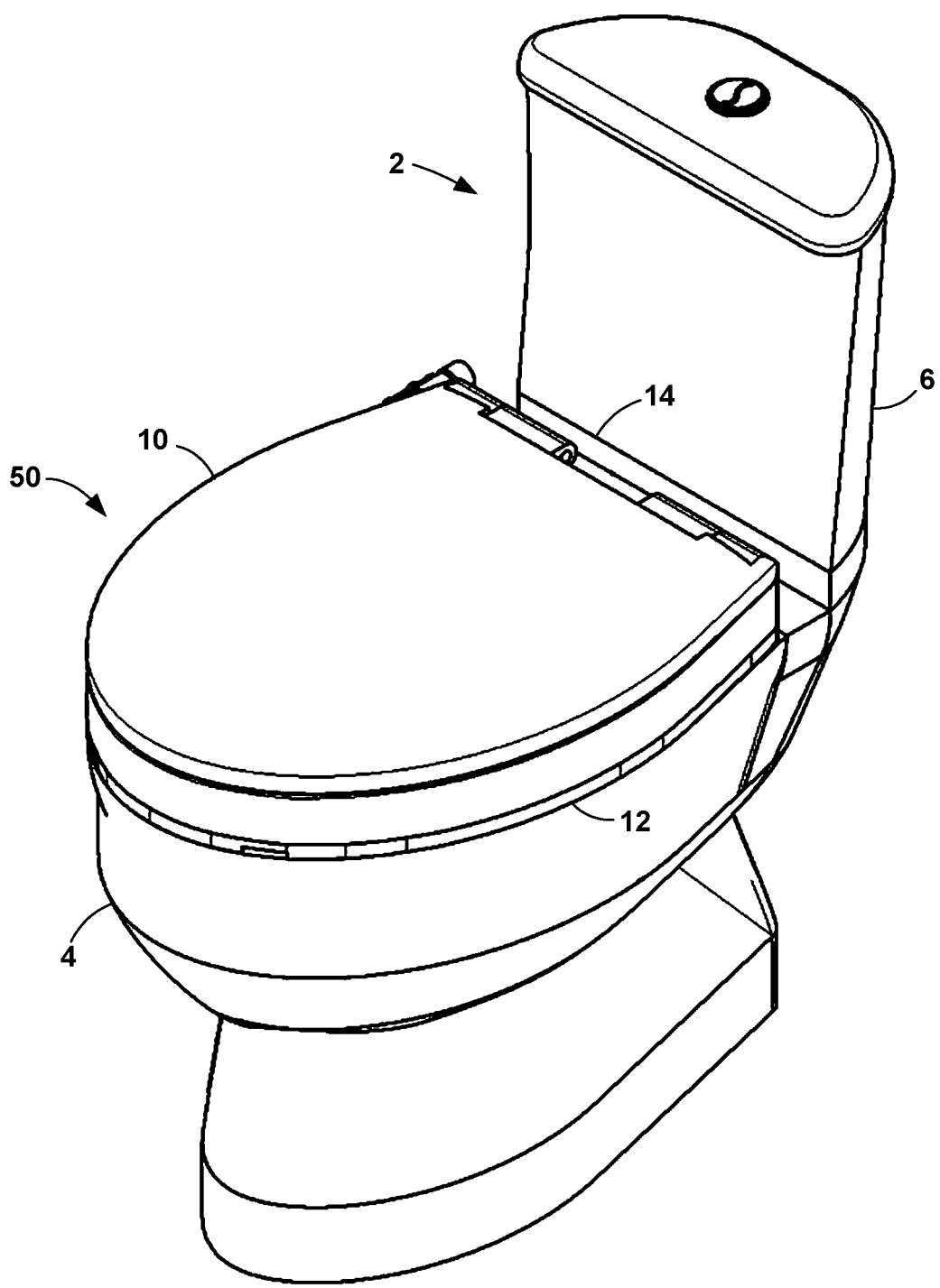
FIG. 1 is a perspective view of the apparatus of the present invention mounted to a toilet with the seat and cover down.
Figure 2:
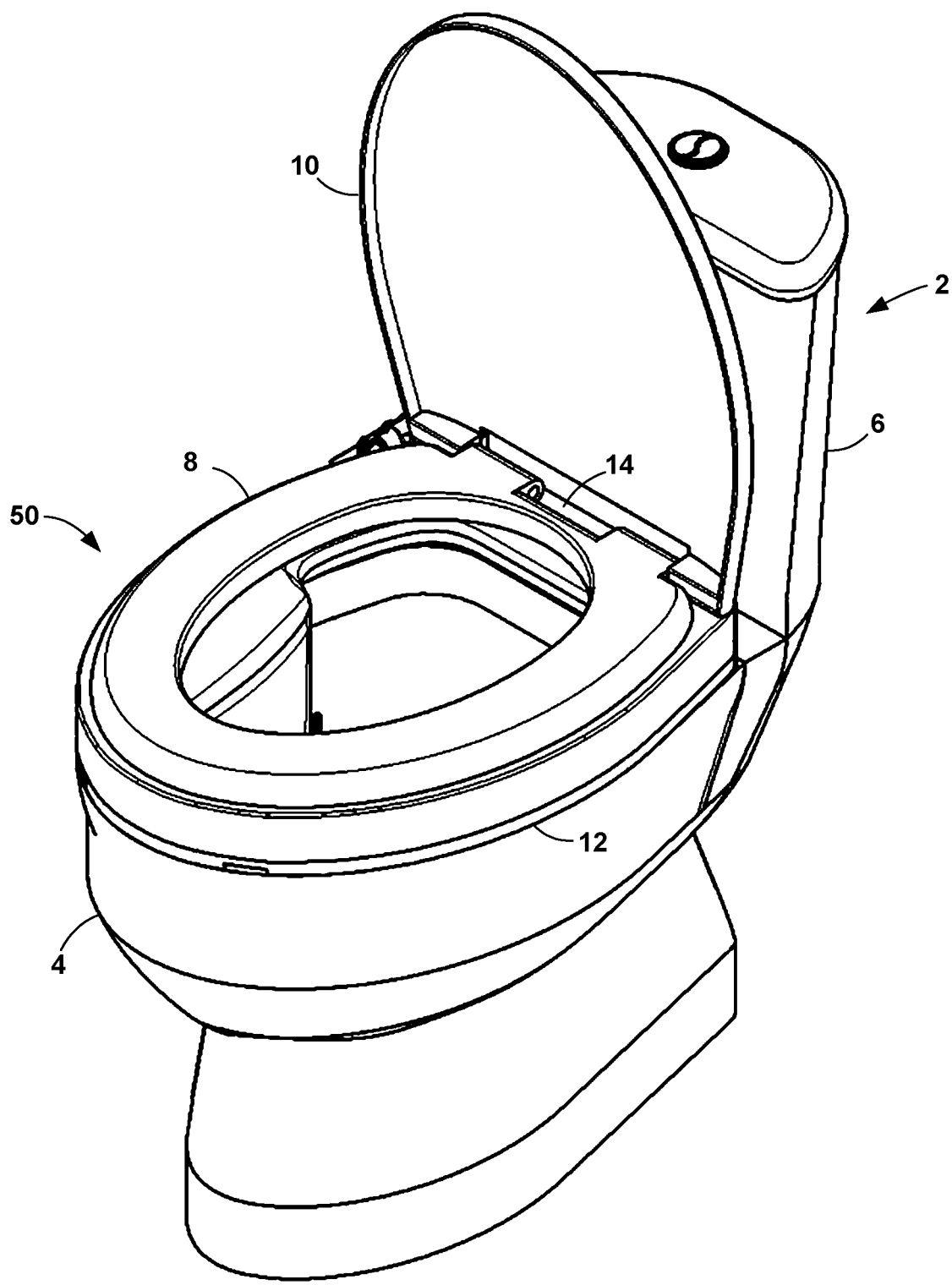
FIG. 2 is a perspective view of the apparatus of the present invention mounted to a toilet with the seat down and cover up.
Figure 3:
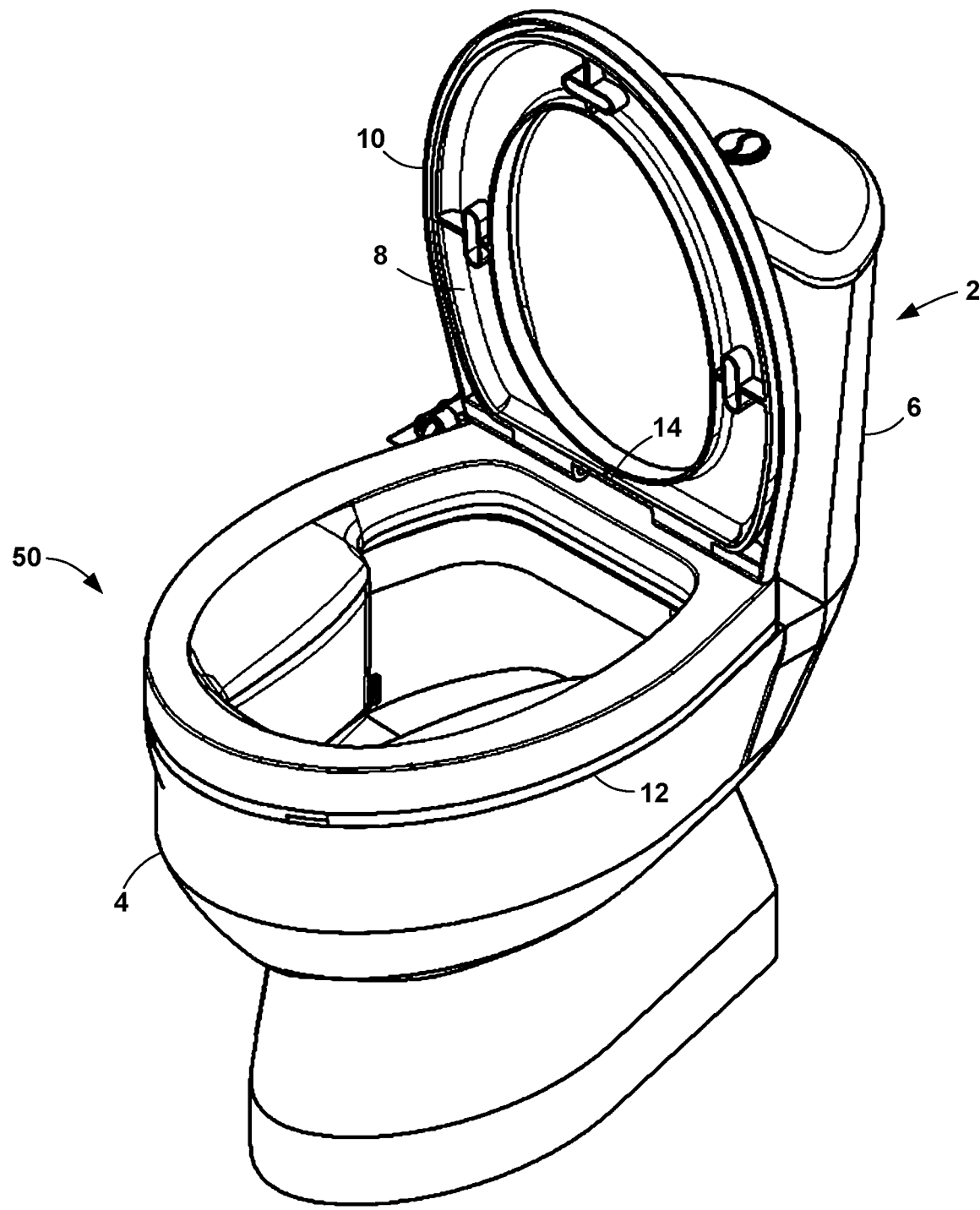
FIG. 3 is a perspective view of the apparatus of the present invention mounted to a toilet with the seat and cover up.

One aspect of the present invention is a urine collecting and analyzing apparatus 50 that mounts to a toilet 2, as shown in FIGS. 1-3. The phrase "mounted to" is intended to encompass both an apparatus integrated into the toilet and an after-market apparatus intended to be installed on the toilet.

The apparatus 50 of the present invention is for conventional or smart toilets 2 that include standard elements: a bowl 4 with a rim 12, a tank 6, and a seat 8. Toilets have bowls 4 that are circular or oval. The apparatus 50 can be adapted for either shape. The toilet 2 can have a cover 10, but it is not necessary for the operation of the present invention.

The apparatus 50 includes a housing 51 with a seat riser 49 and a measurement chamber 52, a urine collecting basin 54, a flushing system 98 to clean the apparatus 50, and a controller 130 in a controller compartment 49 above the measurement chamber 52 for data processing and transmission.

The housing 51 either mounts to or is integrated into the rim 12 of the toilet bowl 4. When integrated, the housing 51 is an internal component of the toilet 2 and operates as the rim 12 of the bowl 4. Optionally, it provides an increase in the height of the rim 12.

When mounted to the toilet bowl 4, the riser 49 sits on the rim 12 of the bowl 4 and provides an increase in the height of the rim 12. It follows the perimeter of the rim 12, extends inwardly over the bowl 4, and has an open center 70 to provide access to the bowl 4. The housing 51 has optional round and elongated shapes that can fit different toilets.

Figure 4:
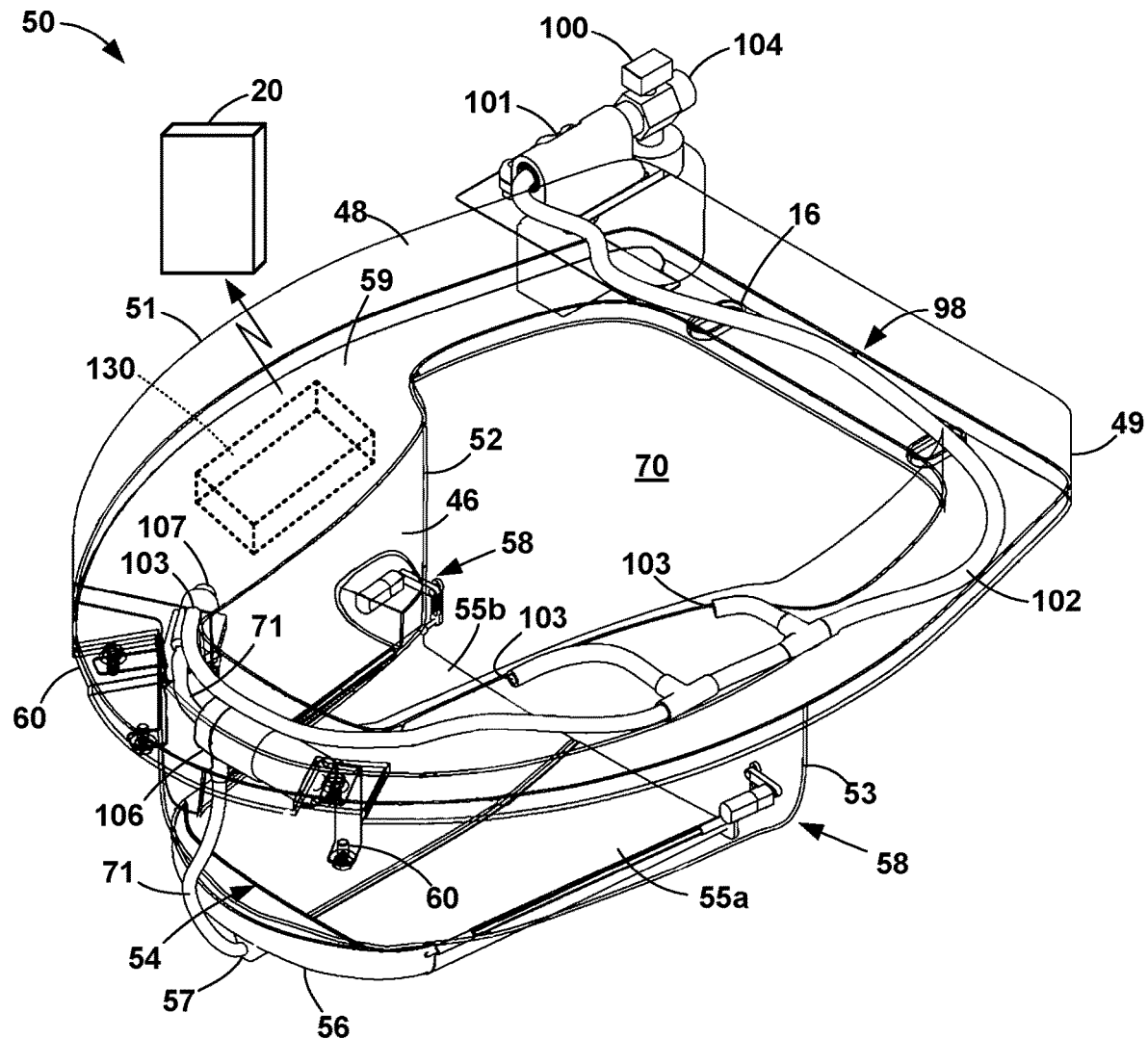
FIG. 4 is a partial phantom view of the device of the present invention.
Figure 5:
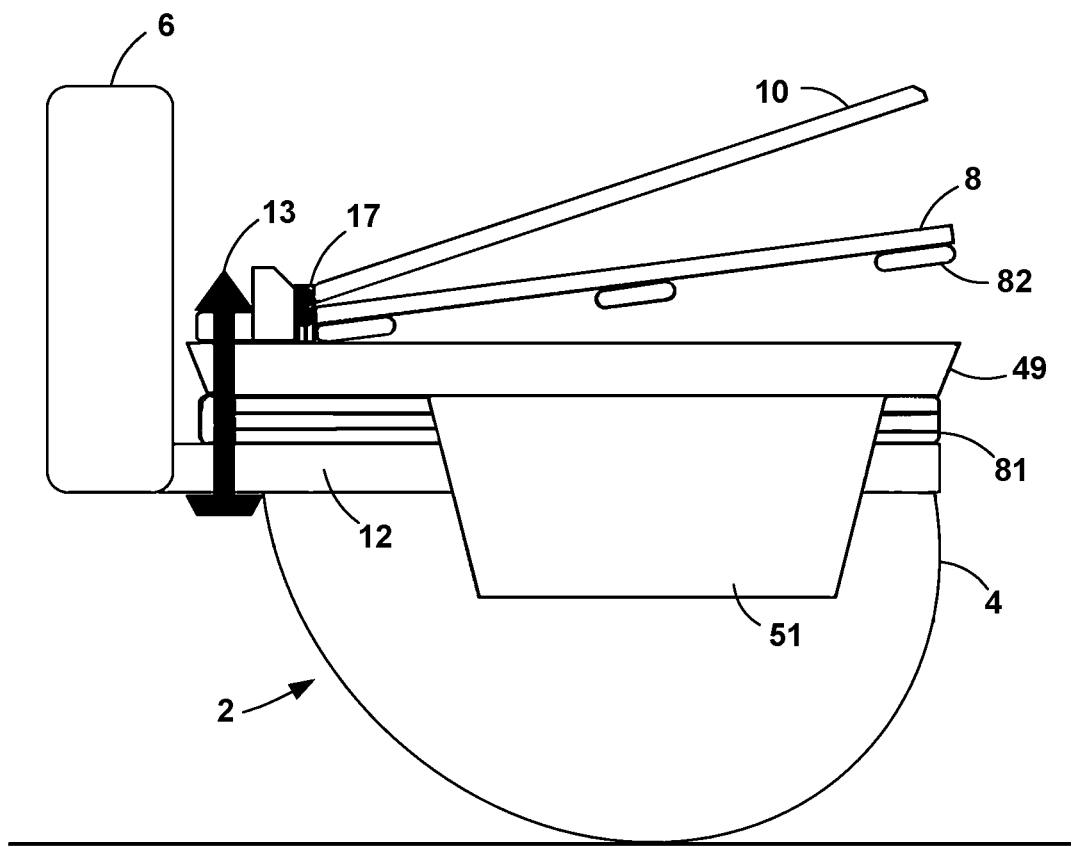
FIG. 5 is a partial cross-sectional side view of the apparatus of the present invention mounted to a toilet.
Figure 6:
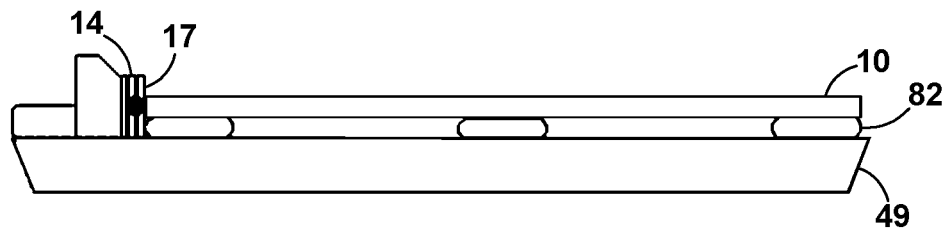
FIG. 6 is a side view with the cushions completely deflated.
Figure 7:
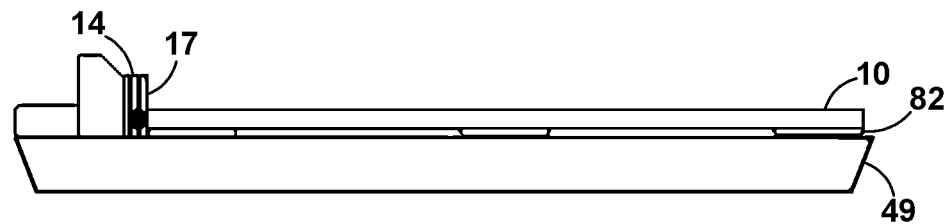
FIG. 7 is a side view with the cushions partially inflated.
Figure 8:
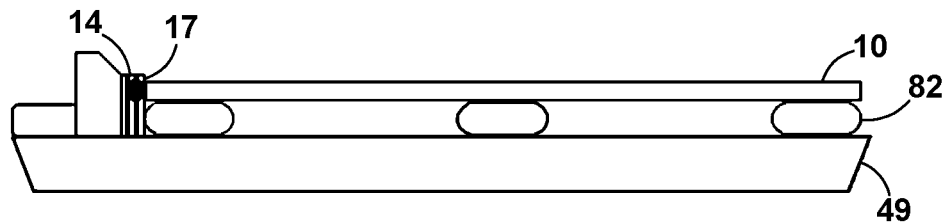
FIG. 8 is a side view with the cushions fully inflated.
Figure 9:
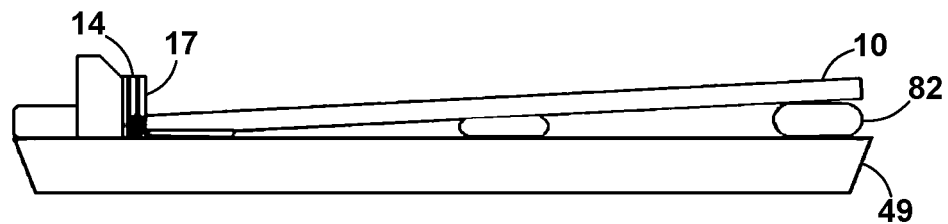
FIG. 9 is a side view with the cushions inflated to slant the seat backward.
Figure 10:
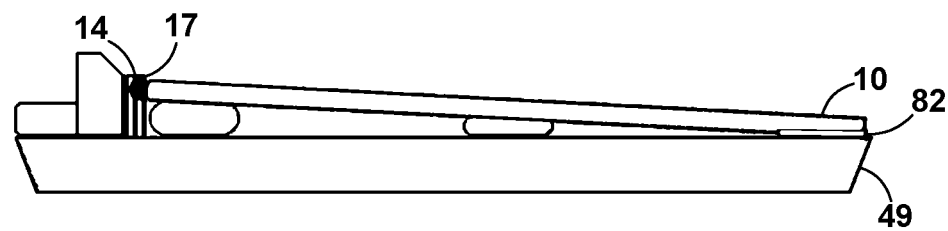
FIG. 10 is a side view with the cushions inflated to slant the seat forward.

The housing 51 is securely attached to the rim 12 by mounting clips 60 in the front, as seen in FIG. 4, and mounting bolts 13 at the back, as seen in FIG. 5. The mounting bolts 13 are longer versions of the original seat/cover bolts that come with the toilet 2. They can reach and rise above the top of the housing 51 and thus connect the original toilet seat 8 and seat cover 10. An optional adapter accommodates different mounting configurations.

The upper surface 48 of the riser 49 around the rim 12 has a funnel-shaped design to help with contamination drainage and to keep the seating area clean. The housing surface can be composed of or coated with water-repellent and anti-bacteria materials, such as corrosion-resistant aluminum. The upper surface 48 can be easily cleaned with traditional bathroom disinfectants. Alternatively, the water from the flushing system 98, described below, can flow through the upper surface 48 to clean the toilet 2 after each use based on a vortex cleaning design described below.

There is an optional attachable bottom riser, not shown, between the toilet rim 12 and the housing 51. It can be installed during installation to further increase the height of the housing 51. The bottom riser will typically be selected from different fixed height options.

Optionally, a set of toilet seat 8 and cover 10 is provided to install on the toilet 2. Optionally, they can provide further height and attitude adjustment over a typical seat 8 and cover 10. The hinge bolts 13 secure the housing 51 (and the bottom riser if installed), seat 8, and cover 10 to the toilet 2.

Optionally, inflatable cushions 82 are integrated into the bottom of the seat 8, as in FIG. 5-10. The cushions 82 can be inflated/deflated independently to adjust the attitude of the seat 8. For example, inflating all cushions 82 to the same level provides a level height, as in FIG. 6. When the cushions 82 are fully deflated, the seat 8 is in the lowest position, as in FIG. 7. When the cushions 82 are fully inflated, the seat 8 is in the highest position, as in FIG. 8. The seat 8 can be tilted backward by inflating the front cushions more than the rear cushions, as in FIG. 9, and tilted front by inflating the rear cushions more than the front cushions, as in FIG. 10.

The hinge 14 that connects the seat 8 and cover 10 can have a vertical slide 17 that allows the seat 8 (and cover 10) to move up and down freely during height adjustment and tilting.

Optionally, a tool is provided for a user to manually inflate and deflate the cushions 82. In addition, an air compressor can be added to the system for users to adjust the height and tilt.

Optionally, a mechanical leveler can replace the inflatable cushions-based solution to provide more precise adjustment and at a more extensive range/capacity.

The measurement chamber 52 extends downwardly from the bottom of the riser 49 along the toilet bowl 4. The measurement chamber 52 is composed of rigid materials that are impervious to urine, examples of which include plastics, ceramics, and metals. Possible plastics include, but are not limited to, urea-formaldehyde (UF), polyvinyl chloride (PVC), and acrylic.

The urine collecting basin 54 collects the urine released by the user. The basin 54 has a bowl shape to collect some or all of the urine for testing. The basin 54 slopes downwardly to the center and front so that the urine flows to an opening 57 at the front of the basin 54. Optionally, the basin 54 can have different designs for men and women.

Figure 11:
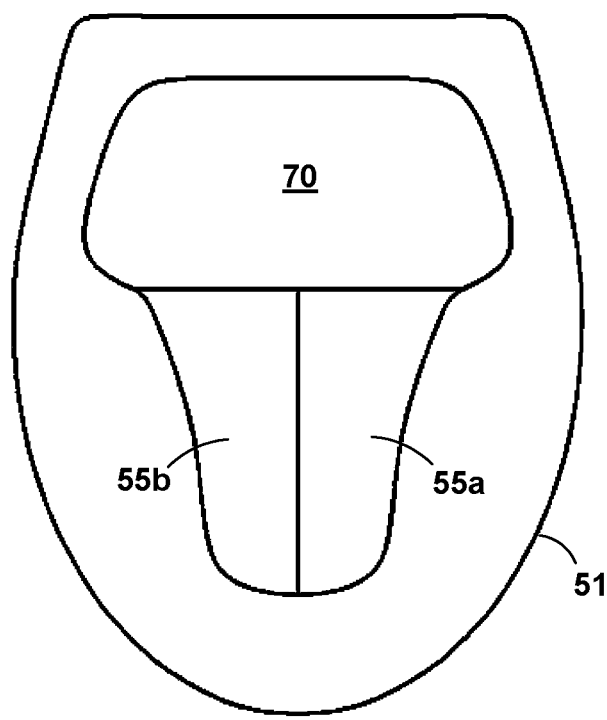
FIG. 11 is a top view showing basin composed of two panels.
Figure 12:
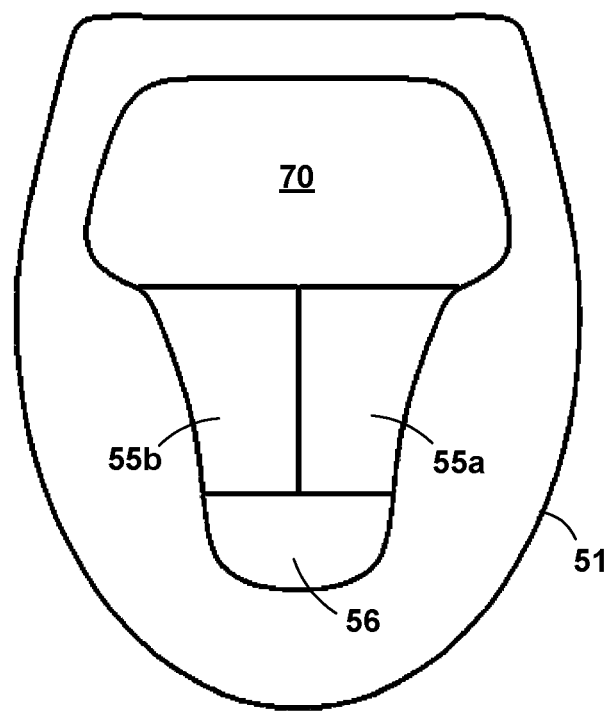
FIG. 12 is a top view of the basin composed of three panels.

The basin 54 is composed of two side panels 55*a*, 55*b* (collectively, 55), as in FIG. 11, or two side panels 55 and a front panel 56, as in FIG. 12. The optional front panel 56 is used to shape the basin 54 for better collecting performance.

The side panels 55 are designed to be stored beneath 47 or along the inner surface 46 of the housing 51 without interfering with everyday toilet usage. The front panel 56 can be mounted in the front beneath the housing 51.

Figure 13:
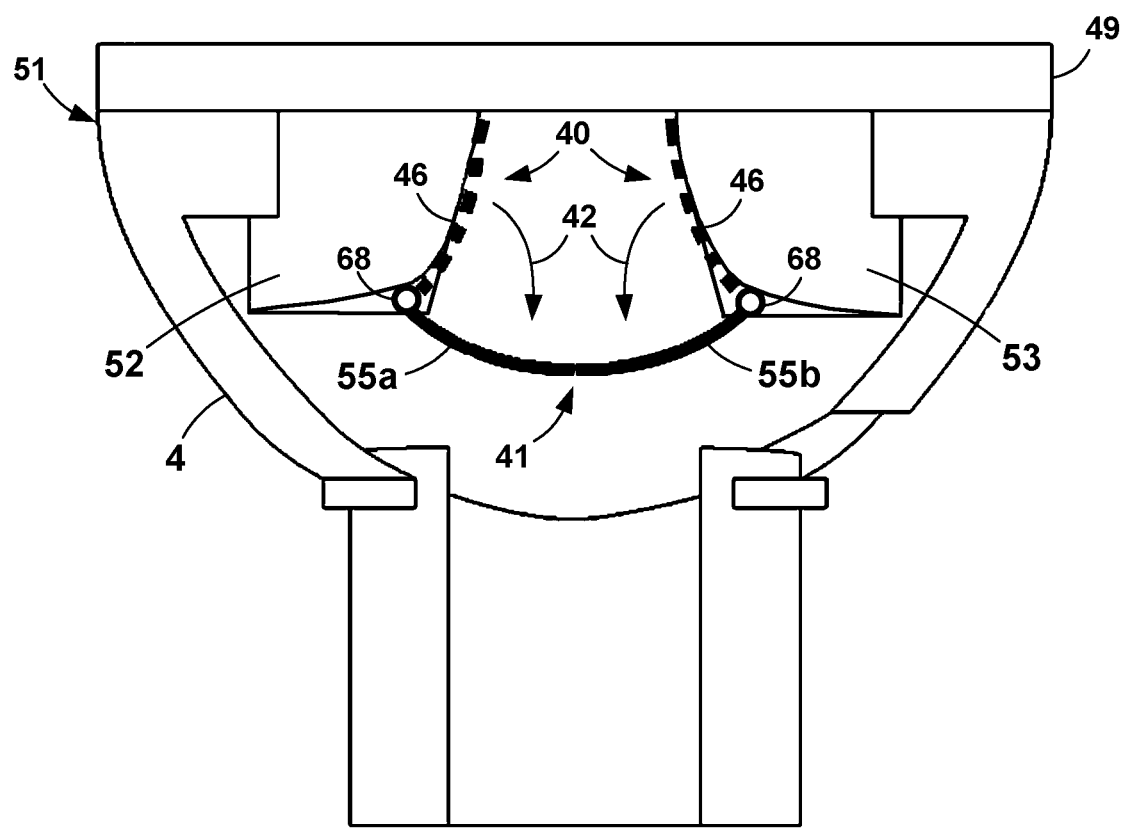
FIG. 13 is a front, cross sectional view showing the lower pivot method of storing the side panels.
Figure 14:
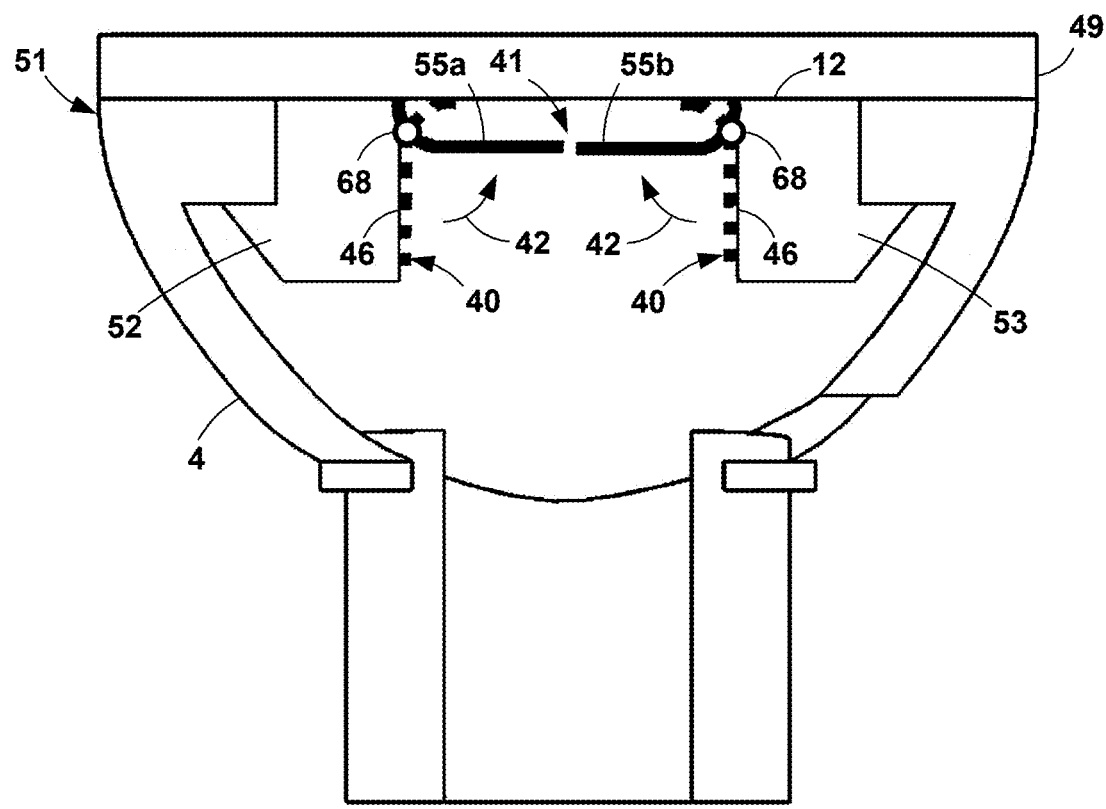
FIG. 14 is a front, cross sectional view showing the upper pivot method of storing the side panels.

The current invention contemplates four different configurations for storing the side panels 55. In the lower pivot configuration of FIG. 13, the two side panels 55 pivot, as at 42, on axles 68 in the lower part of the measurement chamber 52 and auxiliary chamber 53 opposite the measurement chamber 52 between the storage position 40 against the inner surface 46 of the housing 51 and the collecting position 41 below the housing 51. In the upper pivot configuration of FIG. 14, the two side panels 55 pivot, as at 42, on axles 68 in the upper part of the measurement chamber 52 and auxiliary chamber 53 between the storage position 40 against the inner surface 46 of the housing 51 and the collecting position 41 just below the riser 49.

Figure 15:
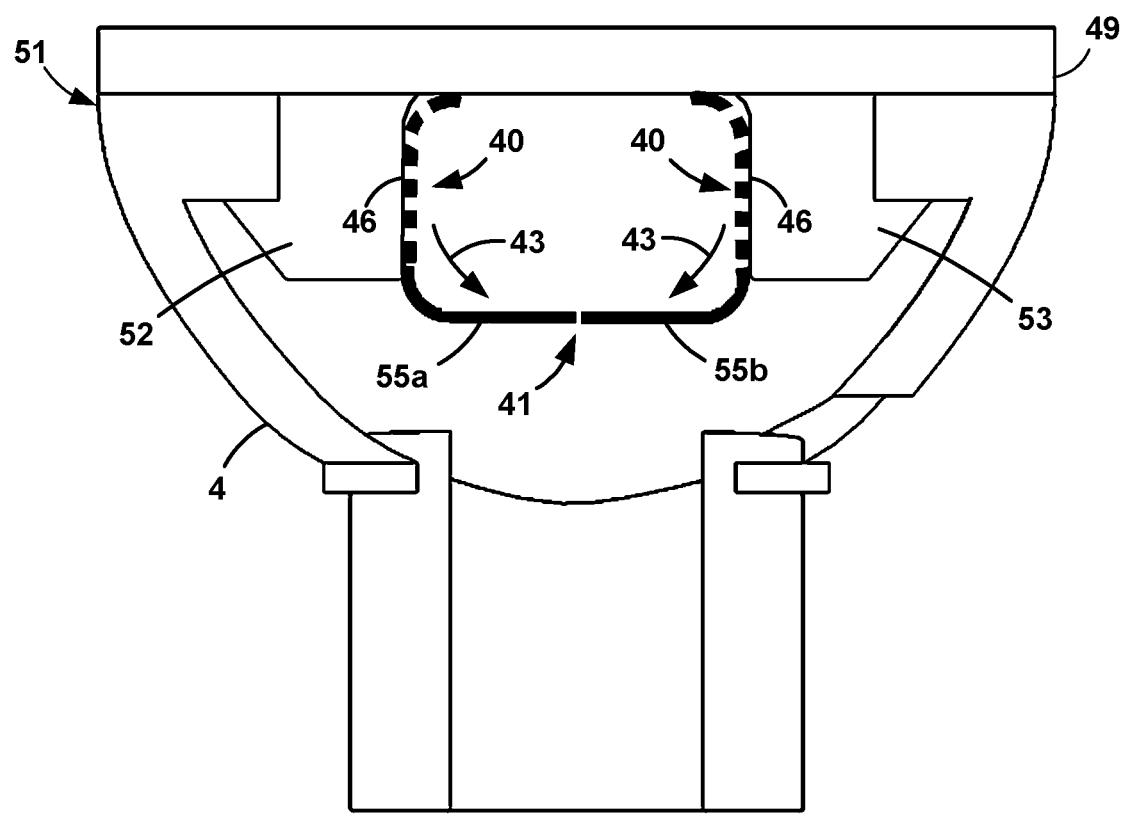
FIG. 15 is a front, cross sectional view showing the side sliding method of storing the side panels.
Figure 16:
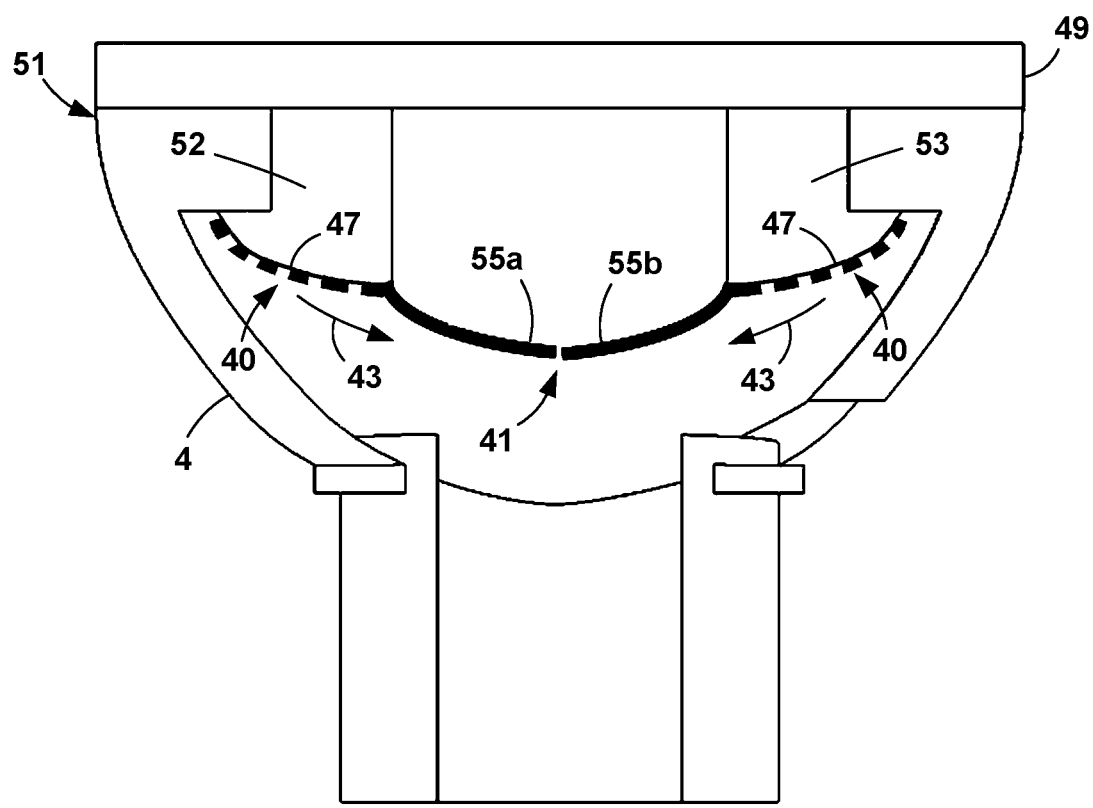
FIG. 16 is a front, cross sectional view showing the bottom sliding method of storing the side panels.

In the side sliding configuration of FIG. 15, the two side panels 55 slide, as at 43, between the storage position 40 against the inner surface 46 of the housing 51 and the collecting position 41 below the housing 51. In the bottom sliding configuration of FIG. 16, the two side panels 55 slide, as at 43, between the storage position 40 against bottom 47 of the housing 51 and the collecting position 41 below the housing 51.

Figure 17:
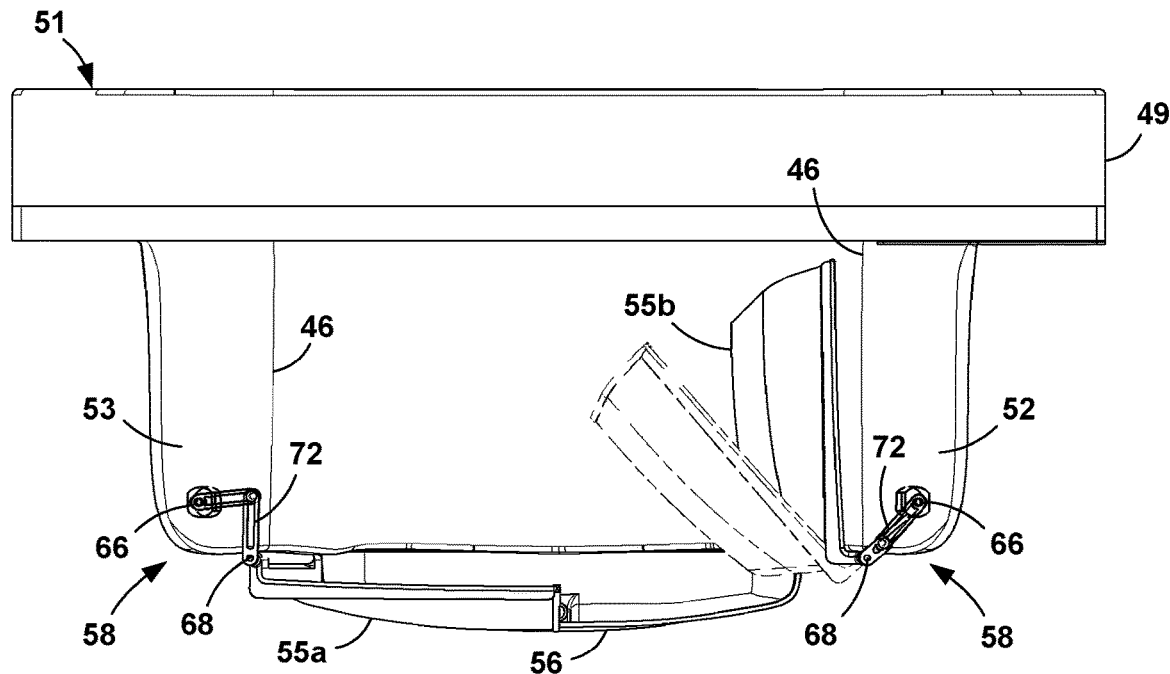
FIG. 17 is a rear detail view of the lower pivot mechanism.
Figure 18:
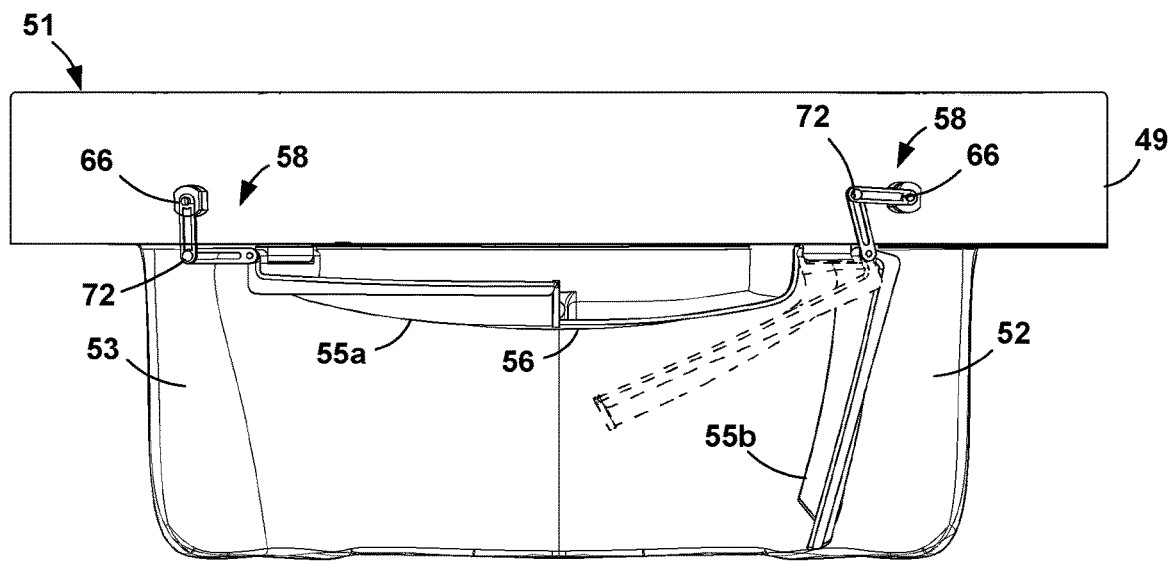
FIG. 18 is a rear detail view of the upper pivot mechanism.
Figure 19:
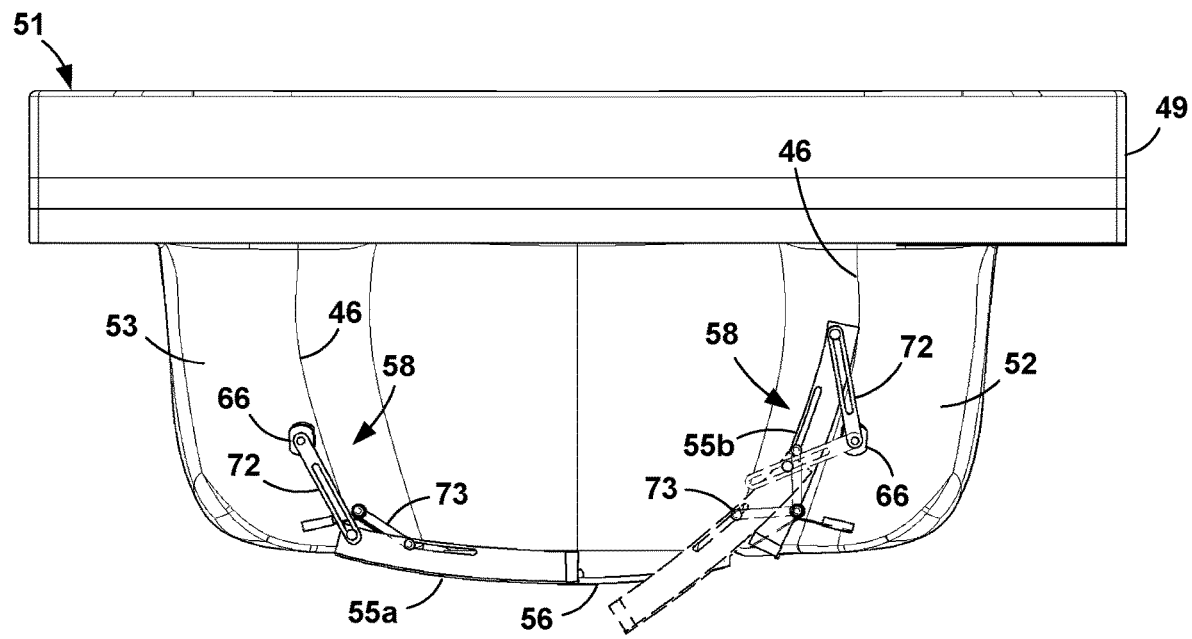
FIG. 19 is a rear detail view of the side sliding mechanism.
Figure 20:
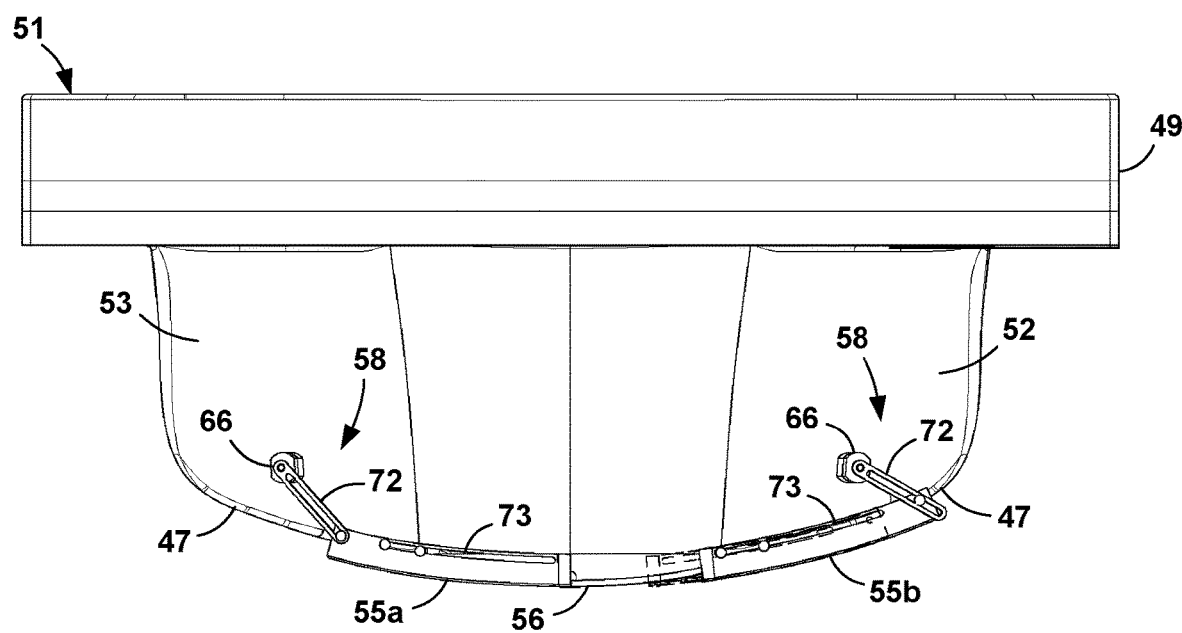
FIG. 20 is a rear detail view of the bottom sliding mechanism.

A motorized basin mechanism 58 moves the panels 55, 56 between the storage position 40 and the collecting position 41. For the lower pivot configuration of FIG. 13, each of the side panel axles 68 is driven by a motor 66 and linkage 72 in the lower part of the measurement chamber 52 and auxiliary chamber 53, as in FIG. 17. For the upper pivot configuration of FIG. 14, each of the side panel axles 68 is driven by a motor 66 and linkage 72 in the riser 49, as in FIG. 18. For the side sliding configuration of FIG. 15, a motor 66 in the measurement chamber 52 and auxiliary chamber 53 drives a linkage 72 that moves the panel 55 along a guide 73, as in FIG. 19. For the bottom sliding configuration of FIG. 16, a motor 66 in the measurement chamber 52 and auxiliary chamber 53 drives a linkage 72 that moves the panel 55 along a guide 73, as in FIG. 20.

Figure 21:
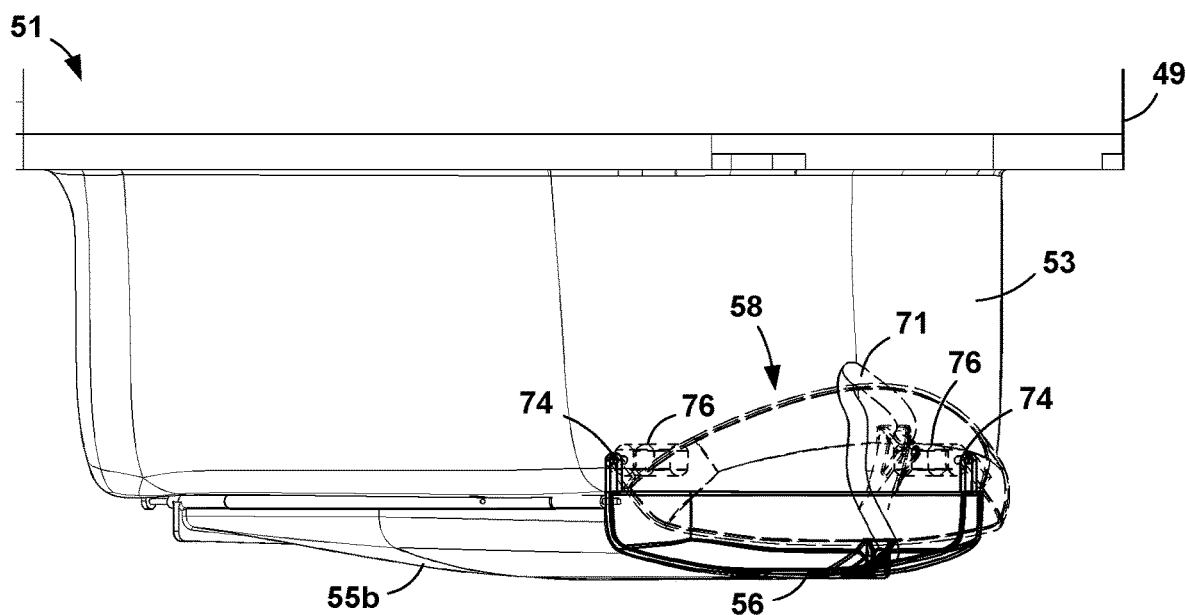
FIG. 21 is a front perspective detail view of the center panel mechanism.

The front panel 56 rotates between the storage position 40 and collecting position 41 on pivot points 74. Motors 76 within the measurement chamber 52 and auxiliary chamber 53 rotate the front panel 56 on the pivot points 74, as in FIG. 21.

Figure 22:
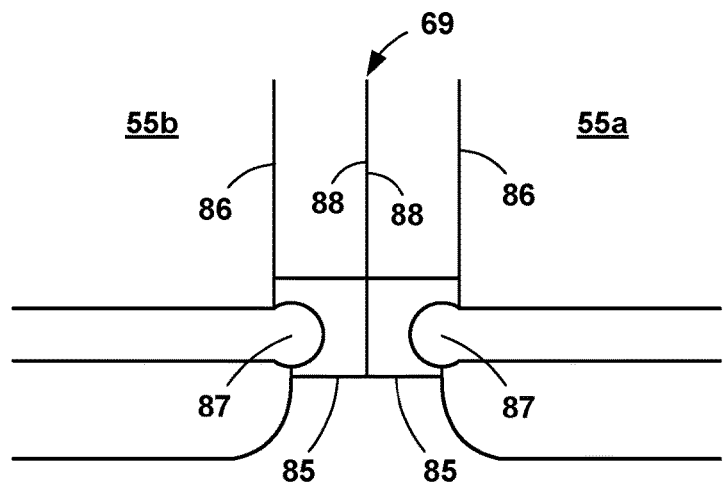
FIG. 22 is a rear, detail view of a magnetic seal between panels.
Figure 23:
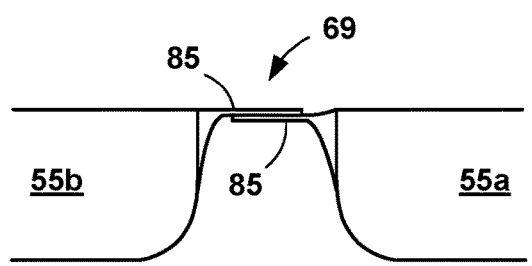
FIG. 23 is a rear, detail view of another magnetic seal between panels.

Rubber seals 69 are affixed to the edges of the panels 55, 56 to seal the panels 55, 56 in the collecting position 41. The seals 69 are rubber flaps 85 attached to the edge 86 of each panel 55, 56. The attachment can take any adequate form, such as adhesive and friction fit. In the configuration of FIG. 22, the flap 85 is attached by snapping it on a cylindrical protrusion 87. Preferably, the rubber flap 85 is magnetized, either by imbedding magnetized particles in the rubber or by attaching a magnet to the rubber flap 85. In one configuration, shown in FIG. 22, the edges 88 of each rubber flaps 85 abut and magnetically adhere to each other. In another configuration, shown in FIG. 23, the rubber flaps 85 overlap and magnetically adhere to each other. In another configuration, not shown, the magnetic flaps 85 adhere to the adjacent panel 55, 56 when the panels 55, 56 are in the collecting position 41. For this configuration, the panels 55, 56 must be composed of a ferrous material. The magnetic attachment ensures a secure and tight fit between the panels 55, 56 so there is no leakage between panels 55, 56.

Figure 24:
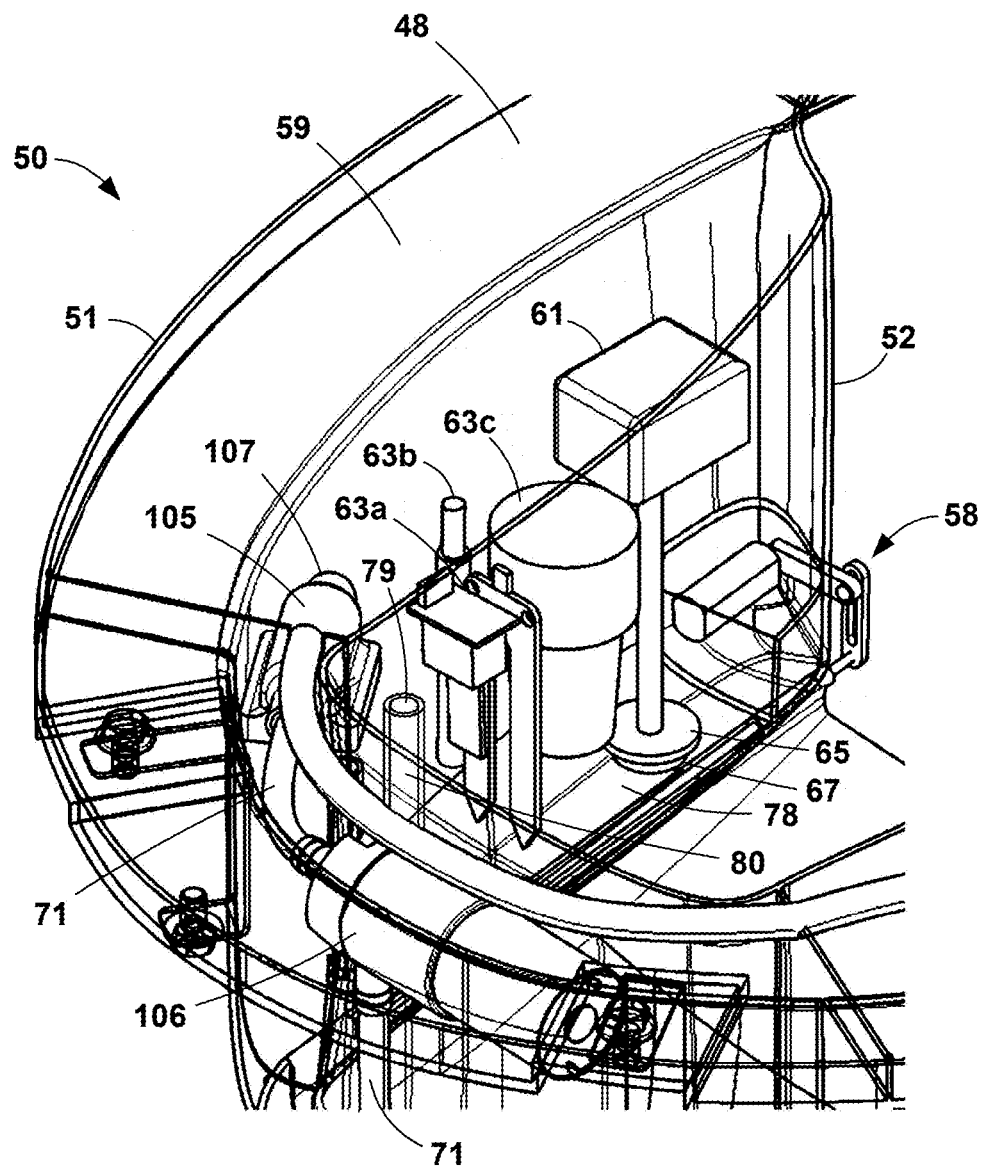
FIG. 24 is a phantom view of the measurement chamber.
Figure 25:
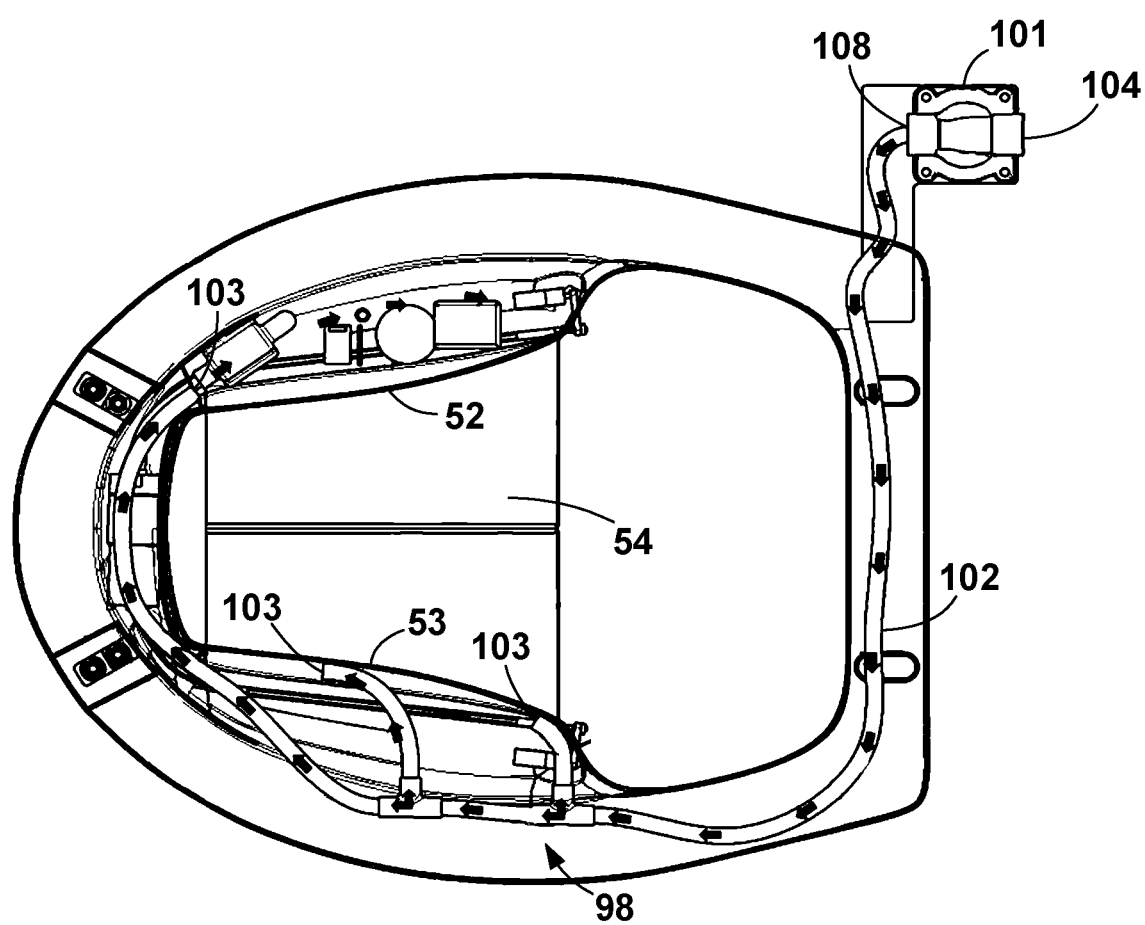
FIG. 25 is a top view of the flushing system.
Figure 26:
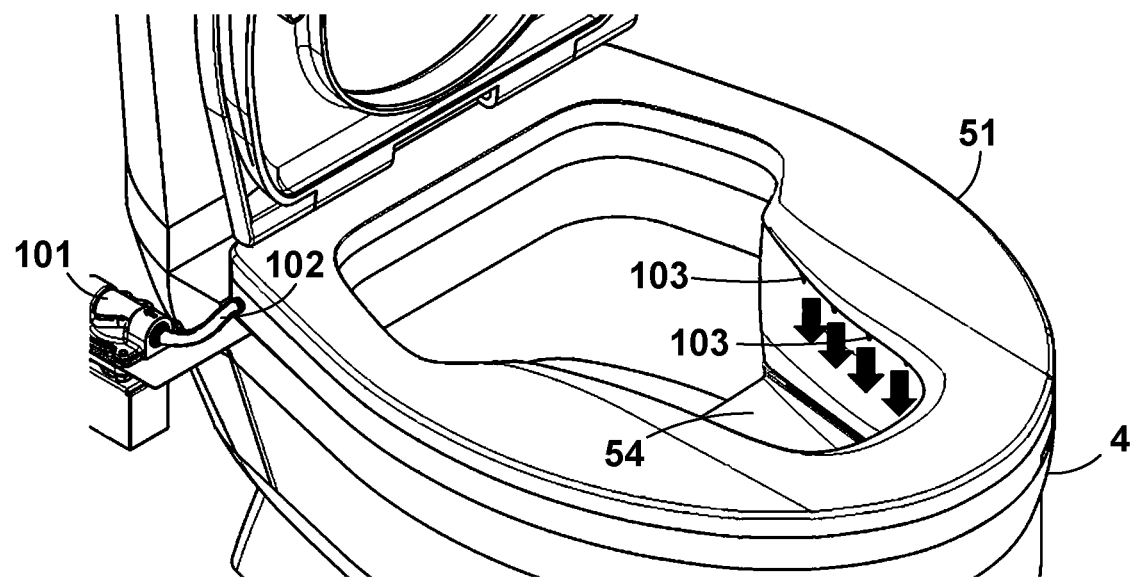
FIG. 26 is a top perspective view of the flushing system.

As shown in FIGS. 4 and 24, a transfer tube 71 extends between the basin 54 and the measurement chamber 52. One end of the tube 71 attaches to the basin 54 at the opening 57. The other end of the tube 71 is attached to an inlet 107 on the top or side of the measurement chamber 52. A flow rate sensor 105 and a pump 106 are in-line with the transfer tube 71. The chamber 52 is sized to ensure that a large enough volume of urine required for accurate measurement can be retained.

The measurement chamber 52 has an overflow outlet 79 to discharge excessive urine. In one configuration, the overflow outlet 79 is a hollow, cylindrical tower 80 rising from the chamber floor 78. Any urine entering the outlet 79 on the top of the tower 80 drains through the tower 80 into the toilet bowl 4.

The chamber 52 has a drain 67 in the floor 78 for draining the chamber 52 into the toilet bowl 4 when testing is complete. A plug 65 operated by a solenoid 61 opens and closes the drain 67. The solenoid 61 is mounted in the controller compartment 59 above the measurement chamber 52 and extends downwardly to the plug 65.

Various sensors dip into the urine collected in the chamber 52 for measurements. The sensors include, but are not limited to, electrochemical sensors 63*a*, temperature sensors 63*b*, pH sensors 63*c* (collectively, 63), urine color sensors, and chromogenic sensors to test for pregnancy, ovulation, or proteins for urinary tract infections.

The apparatus 50 is equipped with a flushing system 98 that flushes water through the system to remove any contaminants that may be present. The flushing system 98 facilitates maintaining optimal performance over an extended period, reducing the need for manual cleaning and maintenance.

The flushing system 98, shown in FIGS. 4 and 25-27, includes a water inlet 104 connected to a water source, typically the line that feeds the toilet 2. The inlet 104 directly feeds a flushing valve 101 mounted to the housing 51. The flushing valve outlet 108 connects to a flushing tube 102 that feeds water to flushing nozzles 103. During flushing, the water is fed through the flushing tube 102 into the basin 54 through the array of flushing nozzles 103 and cleans the entire surface of the basin 54, as in FIG. 26.

Figure 27:
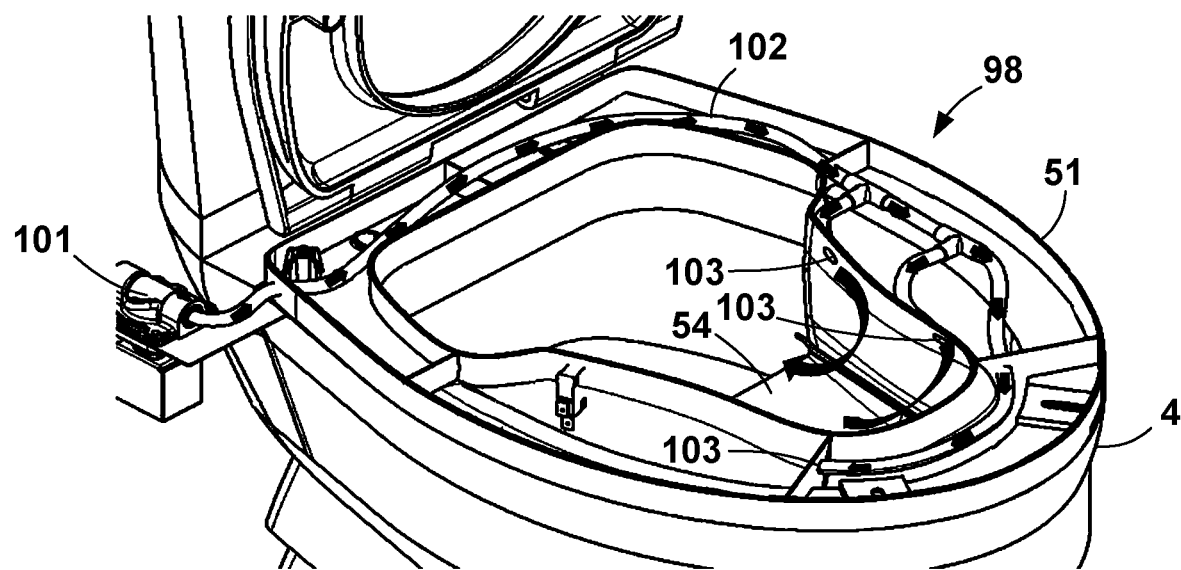
FIG. 27 is a top perspective view of elements of the vortex flushing system.

Alternatively, a vortex flushing design, shown in FIG. 27, can be implemented. More specifically, one or more flushing nozzles 103 with an optional configurable flow rate are installed at the top of the housing 51 above the basin 54, allowing the water to swirl and clean the inside surfaces 46 of the housing 51 and the basin 54. The vortex flushing design achieves maximum cleaning performance with minimum water usage. It propels water streams forward and creates a strong cleaning momentum that effectively cleans the basin 54 and prevents contamination from building up.

Figure 28:
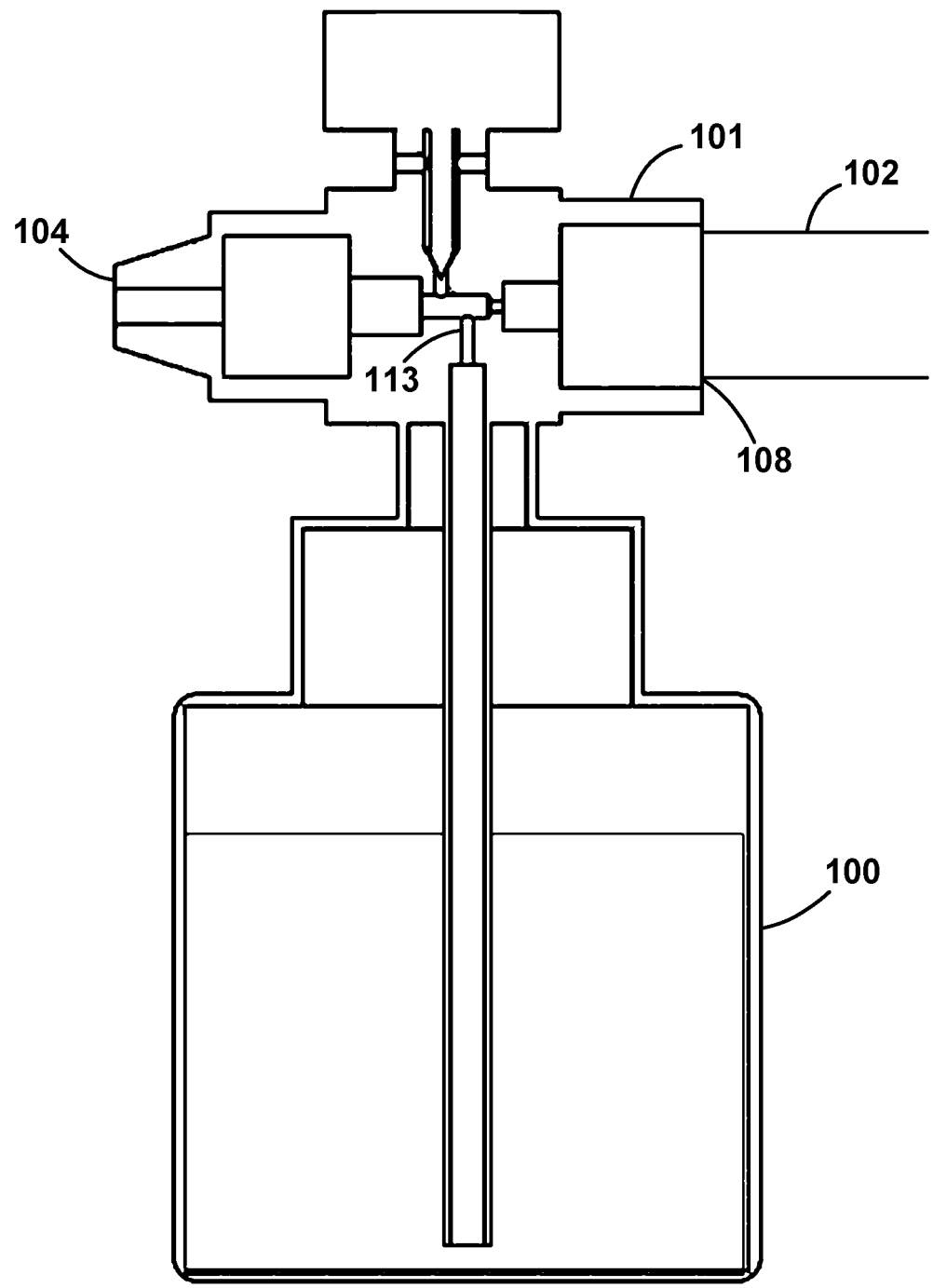
FIG. 28 is a cross-section of the flushing valve with detergent canister.

To further enhance cleaning, an optional detergent canister 100 is attached to the flushing system 98, typically at the flushing valve 101, as shown in FIG. 28. The detergent canister 100 includes a valve 113 that can be opened to inject detergent from the canister 100 indirectly (through the flushing valve 101) or directly into the flushing tube 102, creating a cleaning solution that can more effectively remove contaminants. The detergent canister 100 is refillable or replaceable. The housing 51 is designed to securely hold the detergent canister 100 in place while still enabling the easy access for refill/replacement.

At the beginning of the operation, the system controller 130 optionally determines who the user is by using one or a combination of various identification methods. These methods include, but are not limited to, a set of programmable physical buttons, a fingerprint reader, a proximity sensor that identifies a user's smart and/or wearable devices, a voice analyzer, and an integrated bathroom scale. An optional learning system can be included to improve the identification by learning who the user is.

After the user is identified, the controller 130 prepares the system for testing. The basin mechanism 58 moves the basin panels 55, 56 from their storage position 40 to the collecting position 41 to form the basin 54. The pump 106 in the transfer tube 71 is activated and the system is ready for the user to begin urinating.

As the user urinates, the pump 106 feeds the urine from the basin 54 through the transfer tube 71 to the measurement chamber 52. The flow rate sensor 105 detects the incoming urine, and when urine flow is detected, informs the controller 130, which starts calculating the urine volume. The pump 106 continues feeding the urine from the basin 54 to the chamber 52 until all the urine has passed through. The flow rate sensor 105 detects the start and end of urine flow based on sensed differences between air and liquid.

The controller 130 uses the urine flow rate and volume data to ensure a predetermined minimum volume of urine in the measurement chamber 52 for testing. Alternatively, a liquid level sensor mounted on the measurement chamber wall can detect the urine level, which enables the controller 130 to calculate the volume. The overflow outlet 79 prevents the urine from overfilling the measurement chamber 52. Once urine reaches the minimum volume in the measurement chamber 52 for testing, the controller 130 starts reading the sensors 63. After the desired sensor data is acquired, the controller 130 processes the data and stores the results.

After the data processing is complete, the controller 130 informs the user that the toilet 2 can be flushed. The flushing system 98 is initiated either automatically by the controller 130 by, for example, detecting the toilet flush, or manually by the user, for example, pressing a button to trigger the controller 130 to initiate the flushing system 98.

The drain plug solenoid 61 is activated to open the chamber drain 67 so the urine can drain into the bowl 4, and the flushing valve 101 is opened. If the apparatus 50 includes the detergent canister 100, the detergent valve 113 is opened. Pressure from the water source mixes the detergent and pushes the water through the flushing tube 102 to the flushing nozzles 103. After a predetermined period, the detergent valve 113 is closed.

Meanwhile, the (detergent) water from the flushing nozzles 103 cleans the basin 54. The pump 106 sends the water through the transfer tube 71 into the measurement chamber 52, thereby cleaning the pump 106, flow sensor 105, transfer tube 71, and measurement chamber 52.

After a preset period, the flushing valve 101 is closed and the remaining water continues flowing through the flushing system 98. The pump 106 is stopped after a preset period that can be configured by the user. The controller 130 keeps the drain 67 open for a period of time that permits the remaining water to fully drain and then closes the drain 67.

In the process described above, the pump 106 is controlled directly by the controller 130, that is, the controller 130 turns the pump 106 on and off at predetermined times and intervals. Alternatively, the pump 106 can be controlled by the flow sensor 105, such that, when the flow sensor 105 detects the presence of urine or water, it informs the controller 130 and the controller 130 turns the pump 106 on. When the flow sensor 105 detects that the urine or water has stopped, it informs the controller 130 and the controller 130 turns the pump 106 off. For this method, the flow sensor 105 must be positioned under the basin 54 so gravity causes the urine to flow into the flow sensor 105.

After the flushing system 98 is finished, the controller 130 triggers the basin mechanism 58 to retract the basin panels 55, 56 to their storage positions 40. The apparatus 50 is then deactivated and enters standby mode waiting for the next use.

Optionally, the controller 130 can periodically initiate the flushing system 98 for routine cleaning. Optionally, the controller 130 can learn a user's sleep habits and perform a pre-test flush every morning before the user wakes up.

When the controller 130 finishes processing the data, it sends the assessment results, typically wirelessly, to an app on an external device 20. Typically, the external device 20 is a user's mobile phone. The user is notified when the test is ready to review in the app.

Thus, it has been shown and described an apparatus and method for collecting and testing urine samples. Since certain changes may be made in the present disclosure without departing from the scope of the present invention, it is intended that all matter described in the foregoing specification and shown in the accompanying drawings be interpreted as illustrative and not in a limiting sense.

The invention claimed is:

1. A urine collecting apparatus (50) for a toilet (2) having a bowl (4), the apparatus comprising:
   (a) a housing (51) having a riser (49) adapted to mount on the bowl (4), a measurement chamber (52) extending downwardly into the bowl (4), and an opening (70) in a center adapted to make the bowl accessible;
   (b) a plurality of side panels (55) having a storage position (40) along the housing (51) and a collecting position (41) wherein the side panels (55) form a basin (54) adapted to capture urine released by a user;

(c) a transfer tube (71) fluidly connecting the basin (54) to the measurement chamber (52) such that urine flows from the basin (54) into the measurement chamber (52);

(d) a basin mechanism (58) for moving the side panels (55) between the storage position (40) and the collecting position (41), the basin mechanism (58) including, for each side panel (55), an axle (68) on which the side panel (55) pivots and a motor (66) to rotate the axle (68) between the storage position (40) and the collecting position (41), and wherein the storage position (40) is against an inside surface (46) of the housing (51);

(e) sensors (63) extending into the measurement chamber (52) for measuring parameters of the urine; and (f) a controller (130) for reading sensor data, processing the sensor data, and transmitting results of processing the data to an external device (20).

2. The urine collecting apparatus of claim 1 further comprising a flushing system (98) comprising:
(a) a flushing valve (101) controlled by the controller (130) and having an inlet (104) and an outlet (108), the inlet (104) adapted to be fed from a water source;
(b) a flushing tube (102) from the flushing valve outlet (108) to at least one nozzle (103) above the basin (54);
(c) a drain (67) in the measurement chamber (52); and
(d) a drain plug (65) controlled by the controller (130) to open and close the drain (67).

3. The urine collecting apparatus of claim 2 wherein the flushing system (98) further comprises a detergent canister (100) that injects detergent into the flushing tube (102).

4. The urine collecting apparatus of claim 1 wherein the apparatus includes a means for determining whether the predetermined minimum volume of urine has been reached.

5. The urine collecting apparatus of claim 1 wherein the transfer tube (71) includes a flow sensor (105).

6. The urine collecting apparatus of claim 1 wherein the transfer tube (71) includes a pump (106).

7. The urine collecting apparatus of claim 1 wherein the measurement chamber (52) further comprises an overflow outlet (79) to prevent an excess of urine in the measurement chamber (52).

8. The urine collecting apparatus of claim 1 wherein the plurality of side panels is two side panels (55).

9. The urine collecting apparatus of claim 1 wherein the plurality of side panels is two side panels (55) and wherein the basin (54) includes a front panel (56).

10. The urine collecting apparatus of claim 1 further comprising a seal (69) between panels (55).

11. The urine collecting apparatus of claim 10 wherein the seal (69) is magnetic.

12. The urine collecting apparatus of claim 1 wherein the collecting position (41) is below the housing (51).

13. The urine collecting apparatus of claim 1 wherein the collecting position (41) is below the riser (49).

14. The urine collecting apparatus of claim 1 wherein the external device (20) is a mobile device with an app for personalized configuration, control, monitoring, and data storage.

15. A urine collecting apparatus (50) for a toilet (2) having a bowl (4), the apparatus comprising:
(a) a housing (51) having a riser (49) adapted to mount on the bowl (4), a measurement chamber (52) extending downwardly into the bowl (4), and an opening (70) in a center adapted to make the bowl accessible;
(b) a plurality of side panels (55) having a storage position (40) along the housing (51) and a collecting position (41) wherein the side panels (55) form a basin (54) adapted to capture urine released by a user;
(c) a transfer tube (71) fluidly connecting the basin (54) to the measurement chamber (52) such that urine flows from the basin (54) into the measurement chamber (52);
(d) a basin mechanism (58) for moving the side panels (55) between the storage position (40) and the collecting position (41), the basin mechanism (58) including, for each side panel (55), a guide (73) on which the side panel (55) moves and a motor (66) and a linkage 72 to slide the side panel (55) between the storage position (40) and the collecting position (41);
(e) sensors (63) extending into the measurement chamber (52) for measuring parameters of the urine; and
(f) a controller (130) for reading sensor data, processing the sensor data, and transmitting results of processing the data to an external device (20).

16. The urine collecting apparatus of claim 15 wherein the storage position (40) is against the inside surface (46) of the housing (51).

17. The urine collecting apparatus of claim 15 wherein the storage position (40) is against the bottom surface (47) of the housing (51).

18. The urine collecting apparatus of claim 15 further comprising a flushing system (98) comprising:
(a) a flushing valve (101) controlled by the controller (130) and having an inlet (104) and an outlet (108), the inlet (104) adapted to be fed from a water source;
(b) a flushing tube (102) from the flushing valve outlet (108) to at least one nozzle (103) above the basin (54);
(c) a drain (67) in the measurement chamber (52); and
(d) a drain plug (65) controlled by the controller (130) to open and close the drain (67).

19. The urine collecting apparatus of claim 18 wherein the flushing system (98) further comprises a detergent canister (100) that injects detergent into the flushing tube (102).

20. The urine collecting apparatus of claim 15 wherein the apparatus includes a means for determining whether the predetermined minimum volume of urine has been reached.

21. The urine collecting apparatus of claim 15 wherein the transfer tube (71) includes a flow sensor (105).

22. The urine collecting apparatus of claim 15 wherein the transfer tube (71) includes a pump (106).

23. The urine collecting apparatus of claim 15 wherein the measurement chamber (52) further comprises an overflow outlet (79) to prevent an excess of urine in the measurement chamber (52).

24. The urine collecting apparatus of claim 15 wherein the plurality of side panels is two side panels (55).

25. The urine collecting apparatus of claim 15 wherein the plurality of side panels is two side panels (55) and wherein the basin (54) includes a front panel (56).

26. The urine collecting apparatus of claim 15 further comprising a seal (69) between panels (55).

27. The urine collecting apparatus of claim 26 wherein the seal (69) is magnetic.

28. The urine collecting apparatus of claim 15 wherein the collecting position (41) is below the housing (51).

29. The urine collecting apparatus of claim 15 wherein the collecting position (41) is below the riser (49).

30. The urine collecting apparatus of claim 15 wherein the external device (20) is a mobile device with an app for personalized configuration, control, monitoring, and data storage.

* * * * *